(12) United States Patent
Kolster et al.

(10) Patent No.: US 8,542,440 B2
(45) Date of Patent: Sep. 24, 2013

(54) TUBE FOR AN OBSERVATION DEVICE

(75) Inventors: Nadine Kolster, Aalen (DE); Alfons Abele, Schwaebisch Gmuend (DE); Christian Luecke, Oberkochen (DE)

(73) Assignee: Carl Zeiss Meditec AG, Jena (DE)

( * ) Notice: Subject to any disclaimer, the term of this patent is extended or adjusted under 35 U.S.C. 154(b) by 1017 days.

(21) Appl. No.: 12/378,595

(22) Filed: Feb. 17, 2009

(65) Prior Publication Data

US 2009/0244704 A1  Oct. 1, 2009

(30) Foreign Application Priority Data

Feb. 15, 2008  (DE) .......................... 10 2008 009 303

(51) Int. Cl.
*G02B 21/00* (2006.01)
*A61B 19/00* (2006.01)
*G02B 21/24* (2006.01)

(52) U.S. Cl.
CPC ............ *A61B 19/5223* (2013.01); *G02B 21/24* (2013.01)
USPC .......................................... 359/384; 359/368

(58) Field of Classification Search
USPC .................................. 359/368, 384, 838, 871
See application file for complete search history.

(56) References Cited

U.S. PATENT DOCUMENTS

| | | | | |
|---|---|---|---|---|
| 4,299,439 A | * | 11/1981 | Stromblad | 359/384 |
| 4,576,450 A | * | 3/1986 | Westphal | 359/384 |
| 5,532,872 A | * | 7/1996 | Sakamoto et al. | 359/384 |
| 5,907,432 A | * | 5/1999 | Hayasaka | 359/384 |
| 6,172,804 B1 | * | 1/2001 | Schuck et al. | 359/384 |
| 6,407,857 B2 | * | 6/2002 | Kawasaki | 359/384 |

FOREIGN PATENT DOCUMENTS

| | | |
|---|---|---|
| DE | 33 05 650 A1 | 8/1984 |
| DE | 34 15 958 A1 | 1/1985 |
| DE | 37 18 843 A1 | 12/1987 |
| DE | 297 07 144 U1 | 4/1997 |
| DE | 197 07 520 A1 | 9/1998 |
| DE | 103 00 456 A1 | 7/2004 |
| DE | 103 16 242 A1 | 10/2004 |
| EP | 1 233 294 B1 | 4/2005 |

OTHER PUBLICATIONS

Office Action dated Oct. 31, 2008 in German Patent Application No. 10 2008 009.3, together with English translation of pp. 2 and 3 thereof.

* cited by examiner

*Primary Examiner* — Thong Nguyen
(74) *Attorney, Agent, or Firm* — Kriegsman & Kriegsman

(57) ABSTRACT

A tube for an optical observation device, in particular for a microscope, with a viewing level that is linearly variable in length and/or height, wherein the tube has an optical light path, in which at least two optical elements are disposed, for example, deflecting elements. The tube can be designed, for example, as a swing-in tube, with a base part, wherein a deflecting element is disposed in the base part so that it can rotate around an axis of rotation, and with an eyepiece support that can swing in relative to the base part, wherein a deflecting element is disposed in the eyepiece support so that it can rotate around an axis of rotation. The optical elements may be disposed so that they can move independently of one another in the optical light path.

14 Claims, 16 Drawing Sheets

TUBE FOR AN OBSERVATION DEVICE

BACKGROUND OF THE INVENTION

The present invention relates to a tube for an observation device. For example, such an observation device may involve, for example, a microscope or similar device.

In a microscope, for example, an operating microscope, the distance of the object plane from the position of the equipment—exit pupil EP (AP) behind the eyepiece, thus the viewing level or eyepiece height, is determined by the equipment configuration of the system components of the microscope, which is dependent on the respective application.

For ergonomic reasons, of course, an individual adaptation of the viewing level to the body height of the user of the microscope, for example, of a surgeon, is extremely advantageous and thus desirable. In the often time-intensive working with the operating microscope, keeping the body of the surgeon relaxed is a very decisive factor for working without tiring.

In addition, it is a decisive factor not to modify disadvantageously the usual standard for the surgeon relative to basic optical parameters, such as, for example, the total magnification, the object-field diameter, the object resolution, the free working distance and the optical imaging quality when the viewing level is changed.

With respect to tubes with variable viewing levels, a large number of different solutions are already known in the prior art.

One proposal for solution, for example, contains a purely mechanical distance variation between the microscope body and the tube.

Another solution is described, for example, in DE 34 15 958 A1. A tube with variable viewing level for optical equipment is disclosed therein, whereby the tube can be rotated into two different positions. Of course, only two adjustments are possible, in which the tube can be swung in and locked. A linear displacement or variation of the tube is not provided.

Another solution results, for example, from EP 1 233 294 B1. In this patent, a switchable, thus stepwise variation of the viewing level is achieved by means of a tube construction with variable structural length. The mechanical variation of the structural length is produced in this case by a telescopically extendable region in the tube. The tube has a variable region in the convergent optical beam path for the change in the optical tube length, which is necessary for this, by displacing the focussing position of the intermediate image. In this variable region, correction lenses or groups of lenses which can be pushed in and out are utilized for varying the optical tube length in a first solution proposal, and correction lenses or groups of lenses which can be swung in and out are employed in a second solution proposal. These correction lenses have positive or negative refractive power and shift the intermediate image generated by the tube optics into the stationary viewing field of the eyepiece, whereby the diameter of the intermediate image, expressed in mm, is limited by the field-of-view number FN (SFZ), by a field stop introduced in the eyepiece. In this way, "approximately the same" image segment, visible and sharp, will be imaged in the eyepiece at the "desired" magnification.

In the described solution proposals, the intermediate image which is produced by the tube and displaced with the additional optics, will then be caused to coincide with the viewing field of the eyepiece by means of a mechanical change in distance in a telescopically extendable region.

In the purely mechanical lengthening of the afocal beam path between the components, with increasing change in distance, increasing vignetting also must be taken into account, thus a decrease in brightness from the center of the image field to the edge of the image field or even a cropping at the edge of the image field. In fact, in this approach to a solution, the basic optical parameters are not changed, but one must accept a more or less pronounced reduction in image quality due to the vignetting.

The high mechanical expenditure for the optical correction mechanism comprised of swung-in or pushed-in lenses must be viewed as an essential disadvantage of EP 1 233 294 B1. The space required for this is also problematical, since it leads to a clearly higher structural volume.

Another type of tube involves so-called "swing-in tubes". Swing-in tubes are already known in and of themselves from the prior art. A swing-in tube for an optical observation apparatus, e.g., a microscope, is known, for example, from DE 197 07 520 A1. The swing-in tube provides a base part as well as an eyepiece support, wherein the swinging movement is executed by rolling the eyepiece support out onto the base part along an arc of a circle. A tilted mirror is provided mounted in a rotatable manner around an axis of rotation in the base part, whereby this tilted mirror is forcibly rotated by the roll-out movement of the eyepiece support on the base part. A tilted mirror mounted in a rotatable manner around an axis of rotation is likewise provided in the eyepiece support, whereby this tilted mirror also is forcibly rotated by the roll-out movement of the eyepiece support on the base part.

In this known solution, the swinging of the mirror is always coupled with the roll-out movement. In this way, the two mirrors each move while swinging under the same angle and are coupled with one another. The exit pupil can be swung in a swinging range of ±60° with the known solution. This swinging range that can be executed, however, is insufficient for many applications.

A swing-in tube is described in DE 103 16 242 A1, which can be swung by 180° and thus is named a 180° swing-in tube. For this purpose, the swing-in tube has a first optical element in the form of a prism, which can make an excursion out from a horizontal position by 45° to the top and to the bottom, respectively. Relative to this, another prism can simultaneously also move by 45° each time [to top and bottom] in a second axis. Together, the required angle of ±90° then results therefrom.

In many known solutions, the swing-in tube having a direct view is built too long, particularly for certain applications (for example, in neurosurgery, while in so-called face-to-face applications with a viewing angle (which is the diverging angle of the orthogonal line to the microscope axis) of 15° to 30°, the tube is built too short. Among other things, this means that the distance to the microscope axis is too short. The latter case particularly concerns applications in opthalmoscopy.

SUMMARY OF THE INVENTION

Starting from the named prior art, the problem of the present invention is to provide a tube for an observation device, particularly for a microscope, by means of which different viewing positions or different structural lengths and structural heights of the tube can be realized for any viewing angle.

The problem is solved according to the invention by a tube for an optical observation device, in particular for a microscope, having a viewing level that is linearly variable in length and/or height, wherein the tube has an optical light path, in which at least two optical elements are disposed, hereby characterized in that at least two optical elements are disposed so that they can move independently of one another in the optical light path. The problem is also solved according to the invention by or a tube for an optical observation device, in particular for a microscope, having a viewing level that is linearly variable in length and/or height, wherein the tube has an optical light path, in which at least two optical elements are disposed, in particular so that they can move independently of one another in the optical light path, hereby characterized in that the tube is designed so that it is variably adjustable in its mechanical length. Other features, details, aspects, advantages and effects of the invention result from the subclaims, the description, as well as the drawings.

According to the invention, a tube for an optical observation device, in particular for a microscope, is provided, with a viewing level linearly variable in length and/or height, wherein the tube has an optical light path, in which at least two optical elements are disposed. It is provided according to the invention that at least two optical elements are disposed so they can be moved independently of one another in the optical light path.

According to the present invention, at least two optical elements shall be provided, whereby the invention is not limited to a specific number. More than two such optical elements may also be provided, depending on the configuration. Likewise, the invention is not limited to a specific configuration of the optical elements. Several advantageous, but non-exclusive examples of this will be explained in more detail in the further course of the description.

According to the invention, it is provided that at least two optical elements shall be moved independently of one another, i.e., individually. This includes the case wherein all optical elements can be moved in this way. The case is also included, however, when more than two optical elements are provided and in this case at least one of the optical elements cannot be moved in the named manner.

Likewise, the invention is not limited as to how the individual optical elements can be/shall be moved. For example, they may be rotated and/or displaced. Any combinations thereof are also conceivable, e.g., at least one optical element is rotated and at least one is displaced. Additionally, at least one optical element may also be provided that cannot be moved.

In an advantageous configuration, it is provided that at least two optical elements are provided, which can be displaced and/or rotated independently of one another.

It can be advantageously provided that the tube is designed in such a way that the optical light path (here, this involves the optical path length of the tube) of the tube changes by less than 30% when the viewing level is changed, e.g., when there is a change in the length of the tube. Advantageously, the optical light path changes by less than 10%, and more preferably, by less than 5%. It is most particularly preferred if the optical light path does not change at all or only changes slightly, i.e., if the optical light path remains constant, or at least approximately constant.

A tube according to the invention could thus also be presented as follows, namely with at least one beam path passing through the tube, wherein at least two optical elements are disposed in the beam path, wherein the tube has a constant or approximately constant optical light path, in which the optical elements are found, and wherein at least two optical elements are disposed so that they can be moved independently of one another.

A tube for an optical observation device, in particular for a microscope, is advantageous, having a viewing level that is linearly variable in length and/or height, wherein the tube has an optical light path, in which at least two optical elements are disposed, in particular a tube according to the invention as described above, which is characterized in that the tube is designed so that it is variably adjustable in its mechanical length. Mechanical length is understood here to be the physical, i.e., the body length of the tube. It thus corresponds to the actual linear extension of the tube. The mechanical length need not necessarily be identical to the optical wavelength (to the optical light path). It is preferred according to the present invention if the optical wavelength of the tube (its optical light path) does not change or only slightly changes with a mechanical change in the length of the tube.

The advantage of an adjustable tube, in which the optical wavelength does not change with its mechanical change in length (e.g., when it is "pulled out"), lies in the fact that the magnification of the system does not change when the tube is adjusted and that the position of the exit pupil remains constant.

An optical tube for an observation device, in particular for an operating microscope, can be characterized in that its mechanical length (i.e., the distance from the eyepiece to the site of connection with the remainder of the observation device) can be variably adjusted, wherein all essential optical components are or can be installed in fixed manner in the beam path. This means that no optical components are present that must be swung in or reconstructed in order to effect a change in length while maintaining other optical properties.

It may be provided preferably that the change in length can amount to at least 10%, preferably 30%, more preferably 50%, and particularly preferred, at least 100%.

Advantageously, the number of change steps can be greater than 2, preferably greater than 5, more preferably greater than 20, and most particularly preferred, can change continually.

In another configuration, it can be provided that the optical beam path is bent.

As was mentioned also above, the optical elements can be designed in different ways. For example, they may involve lenses, lens systems, lens groups, prisms or the like. Advantageously, at least one optical element can be designed as a deflecting element. The present invention is not limited to specific types of deflecting elements. Advantageously, however, the deflecting elements can be designed as tilted mirrors. The deflecting elements, however, could also generally involve appropriately configured deflecting prisms or the like. Of course, combinations of different optical elements are also conceivable.

It can be advantageously provided that the tube is designed so that it can be linearly displaced. For example, it then can be provided that an optical element is disposed so that it can be displaced parallel to the connection line between the other optical element and the connection to the observation device. Preferably, the displacement movement may lie or may be produced on a straight line. Then at least one optical element (preferably two optical elements) can be disposed so that they can be displaced on a single straight line. The focus can then be adjusted by moving the optical element.

Basically, the tube can be designed so that it has a base element for mounting with the optical observation device. The tube can then be disposed on or fastened to the observation device via the base element.

The present invention is not limited to specific types of observation devices. The observation device may involve, for example, a microscope, e.g., an operating microscope or similar device.

For example, the tube can be configured for a monocular view (one beam path), or also as a binocular tube (two separate beam paths for stereomicroscopy). In the last-named case, the optical elements preferably of both beam paths can be utilized jointly.

In an advantageous configuration, the tube can be designed as a swing-in tube. In a simple design, a double-joint configuration can be provided, in which an eyepiece support is fastened to the base part so that it can be swung in. Triple-joint connections, however, are also conceivable, in which the eyepiece support is disposed on an intermediate support so that it can be swung in and by the latter means is fastened to the base element so that it can be swung in. In a quadruple-joint configuration, the eyepiece support is joined to the base part in a corresponding way by means of two intermediate supports, which are joined one below the other so that they can be swung in.

Advantageously, a swing-in tube for an optical observation device, in particular for a microscope, is provided, with a base part, wherein a deflecting element that can rotate around a first axis of rotation is disposed in the base part and with an eyepiece support that can swing relative to the base part, wherein a deflecting element that can rotate around a second axis of rotation is disposed in the eyepiece support. The swing-in tube is hereby characterized in that the deflecting elements are disposed so that they can rotate and/or be displaced independently of one another.

Such a swing-in tube first consists of a base part as well as an eyepiece support that can be swung in relative to the base part. The swinging in can occur by swinging the eyepiece support around the base part or by swinging the base part around the eyepiece support, or by swinging both the eyepiece support and the base part around one another.

The base part provides a deflecting element for deflecting the beam, which [element] is disposed in the base part so that it can rotate around an axis of rotation. The eyepiece support, which serves for supporting the eyepiece, or the optical elements necessary for this, also provides a deflecting element for deflecting the beam, which is disposed in the eyepiece support so that it can rotate around an axis of rotation.

It is advantageously provided that both deflecting elements can be rotated and/or displaced independently of one another. In particular, an ergonomic swing-in tube can be created thereby, which can be used for multidisciplinary purposes on an observation device, for example, on a microscope. By the use of two deflecting elements that can be rotated or swung in and/or displaced independently of one another, different, ergonomic viewing positions or structural heights and structural lengths of the swing-in tube can be realized for nearly any viewing angle.

Thus, in an advantageous configuration with a direct view (pivoting angle of 0°), a variation of the structural length of ±30 mm is possible, for example.

Likewise, viewing angles of more than 90°, for example, up to 100°, can be realized.

This is particularly achieved by the fact that the rotating or swinging movement of the two deflecting elements is no longer directly coupled, as was the case, for example, for the solution described in DE 197 07 520 A1.

Advantageously, the optical elements, e.g., the deflecting elements, contain a translatory component.

In another configuration, the deflecting elements may be disposed so that they can swing, but are also rotationally independent of one another. This means that the two deflecting elements can be rotated or swung in and displaced completely independently of one another, wherein, in addition to the movement on an arc of a circle, another linear component of motion also exists.

Preferably, the eyepiece support can be disposed so that it can swing on the base part via at least one intermediate support. The invention is not limited to specific embodiments of the intermediate support, however. This support preferably has a lengthwise extended form, whereby "lengthwise extended" means that the intermediate support has a greater length than width. Here also, the invention is not limited to a specific number of intermediate supports. For example, two or more intermediate supports may also be provided.

In another configuration, the intermediate support may be joined to the base part by means of a rotating joint. Alternatively or additionally, the intermediate support can also be joined with the eyepiece support by means of a rotating joint. The invention is not limited to specific types of rotating joints. If two or more intermediate supports are provided, these can also be joined together via a rotating joint.

Advantageously, the deflecting element of the base part and/or the deflecting element of the eyepiece support can be disposed in the region of a rotating joint.

It is of particular advantage if an appropriate coupling is provided here. Thus, it can be preferably provided that the deflecting element of the base part is coupled with the rotating joint between the base part and the intermediate support. Alternatively or additionally, it may advantageously be provided that the deflecting element of the eyepiece support is coupled with the rotating joint between the eyepiece support and the intermediate support. The coupling can be accomplished in the most varied manner, so that the invention is not limited to specific coupling mechanisms. For example, the deflecting element can be combined with a coupling element, whereby the coupling element in turn cooperates with a driver element, which is disposed on the rotating bearing.

Advantageously, the deflecting element of the base part and the corresponding rotating joint may have an identical axis of rotation. Alternatively or additionally, the deflecting element of the eyepiece support and the corresponding rotating joint may also have an identical axis of rotation.

Relative to the angle of rotation of the deflecting element and the rotating joint, it may be advantageously provided that the deflecting element of the base part is disposed so that it can rotate around the axis of rotation at an angle of rotation which corresponds to half of the angle of rotation of the rotating joint around the axis of rotation.

In another configuration, it may be provided that the deflecting element of the eyepiece support is disposed so that it can rotate around the axis of rotation at an angle of rotation, which corresponds to half of the angle of rotation of the rotating joint around the axis of rotation.

Advantageously, it may be provided that the axis of rotation of the first deflecting element is disposed parallel to the axis of rotation of the second deflecting element.

In another configuration, it may be provided that at least one optical decoupling element and/or at least one optical coupling element is/are disposed in the base part. In this case, it may advantageously involve divider elements, such as, for example, a splitter cube, a splitter mirror, and similar dividing devices. These elements can be used, for example, in connection with documentation devices, data reflection devices, and similar devices. It can be advantageously provided in this way that these element(s) are used instead of the otherwise often employed glass plate.

Advantageously, optical splitters for the above-named purposes can be provided above a tube mounting surface (for mounting to the optical observation device) in its base part, which makes possible, for example, savings relative to additional optical components. A decoupling device can also be positioned, for example, laterally or toward the back, on a side not facing the observer.

By means of the present invention, an ergonomic tube, for example, a swing-in tube, with variable viewing direction and variable position of the exit pupil will be created.

Advantageously, the exit pupil may involve a diaphragm, or the exit pupil may be designed as a diaphragm. In another configuration, it may be provided that the exit pupil of the eyepiece advantageously lies in a positional range LAP for different viewing angles and/or viewing positions.

In the case of a swing-in tube, it may be provided that by a coupling of the deflecting elements of the base part with the intermediate support or of the intermediate support with the eyepiece support, the two axis of rotation (mirror axes, if the deflecting elements are tilted mirrors) can move independently of one another. In this way, the exit pupil can be moved freely in the positional range. Linear movements are also possible with the same pivoting angle. There is no coupling of the two axes of rotation of the deflecting elements. In contrast, a swing-in tube with variable viewing direction is described in DE 197 07 520 A1, wherein the eyepiece support is forcibly rotated on the base part by a roll-out movement by means of meshing toothed gears. Due to the forced coupling between the base part and the eyepiece support, the two deflecting elements move in a coupled manner and by the same angle when they are swung in.

BRIEF DESCRIPTION OF THE DRAWINGS

In particular, it is also possible, by means of the tube according to the invention, for example, a swing-in tube according to the invention, to be able to realize different viewing positions and/or structural heights and/or structural lengths for any viewing angle, up to the end stops.

In summary, the present invention may also be described, as follows. A tube for an optical observation device, in particular for a microscope, is described, having a viewing level linearly variable in length and/or height, wherein the tube has an optical light path, in which at least two optical elements are disposed, for example, deflecting elements. The tube can be designed, for example, as a swing-in tube, with a base part, wherein a deflecting element that can rotate around an axis of rotation is disposed in the base part and with an eyepiece support that can swing relative to the base part, wherein a deflecting element that can rotate around an axis of rotation is disposed in the eyepiece support. In order to make possible a large swinging range, for which different viewing positions or structural lengths and structural heights of the swing-in tube can be realized simultaneously for any viewing angle, it is proposed according to the invention that the optical elements are disposed so that they can move independently of one another in the optical light path. For example, the deflecting elements can be disposed in a swing-in tube, so that they can be rotated and/or displaced independently of one another.

Figure 12:
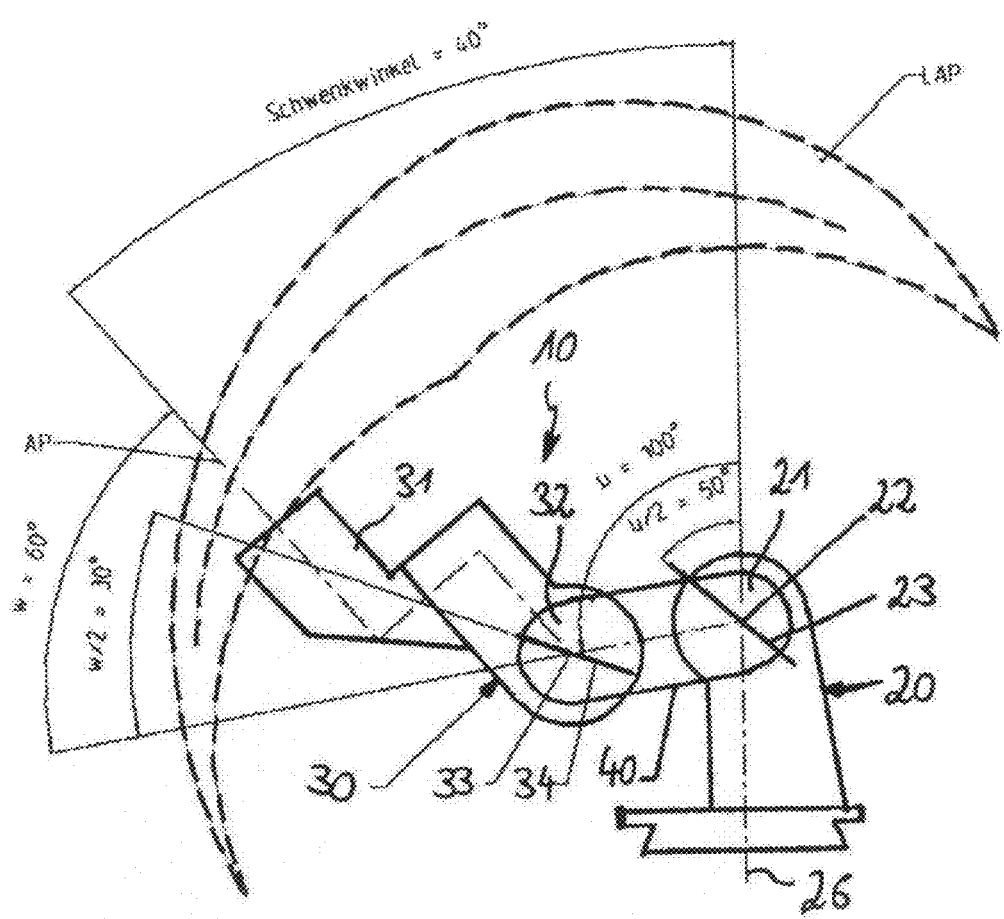
Figure 13:
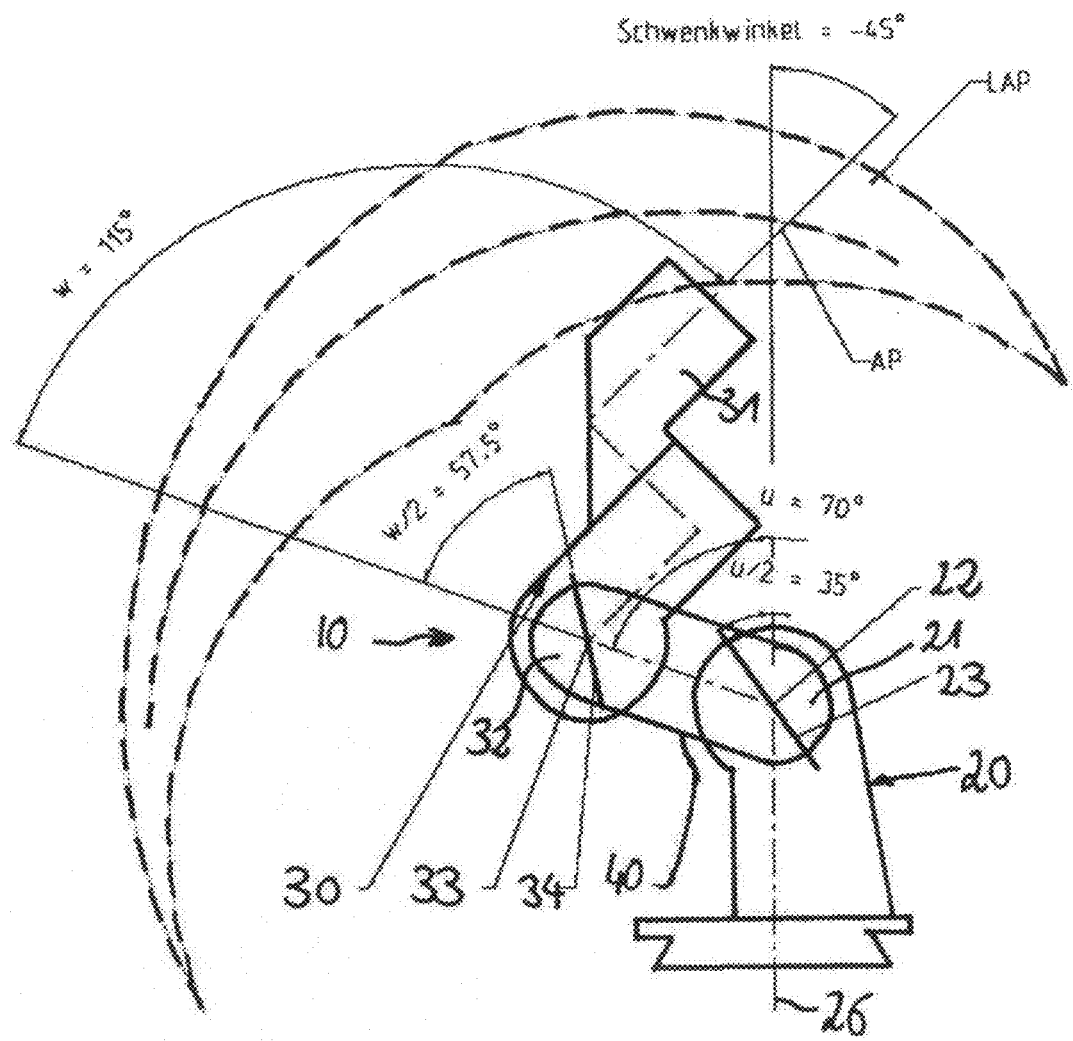
Figure 14:
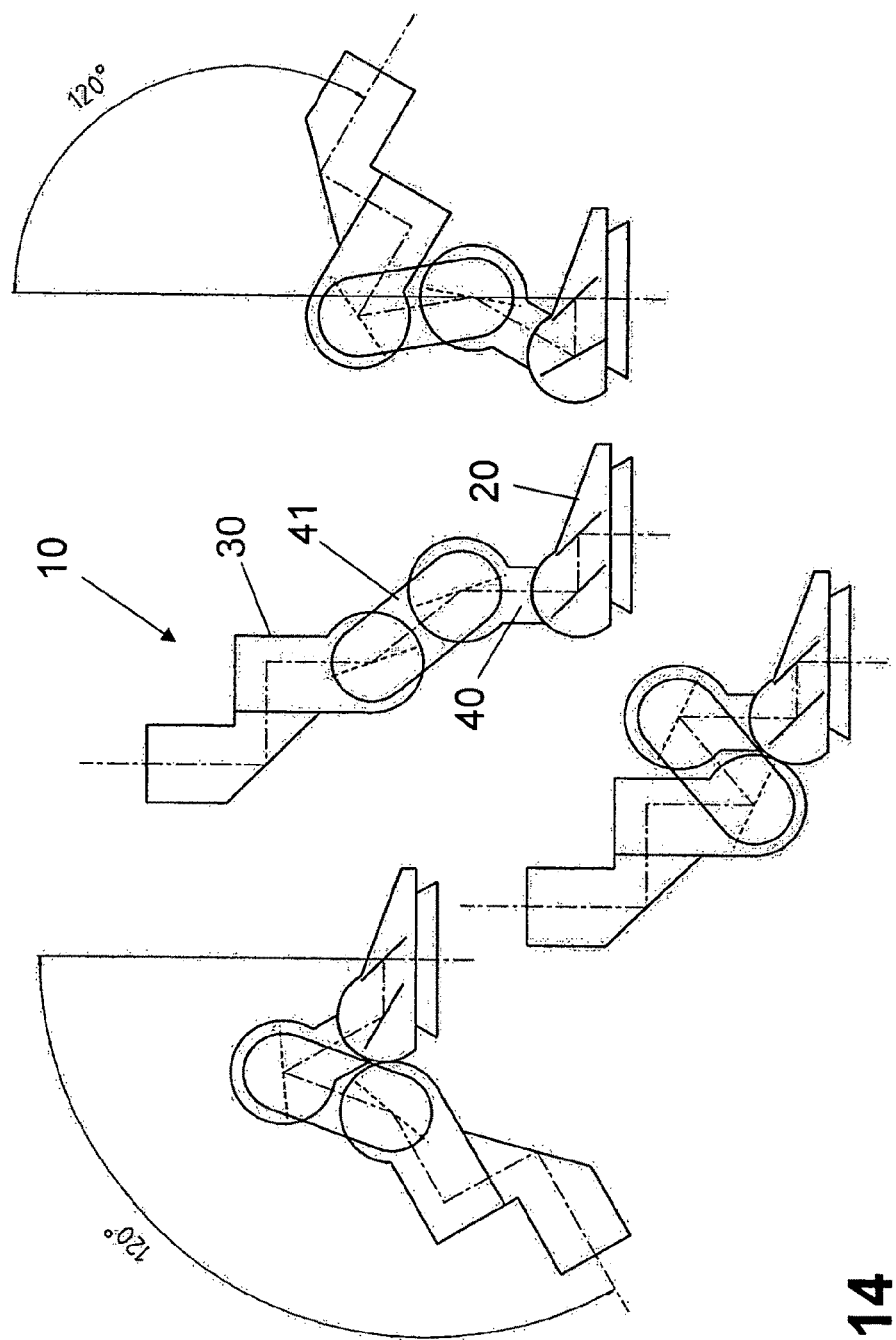
Figure 15:
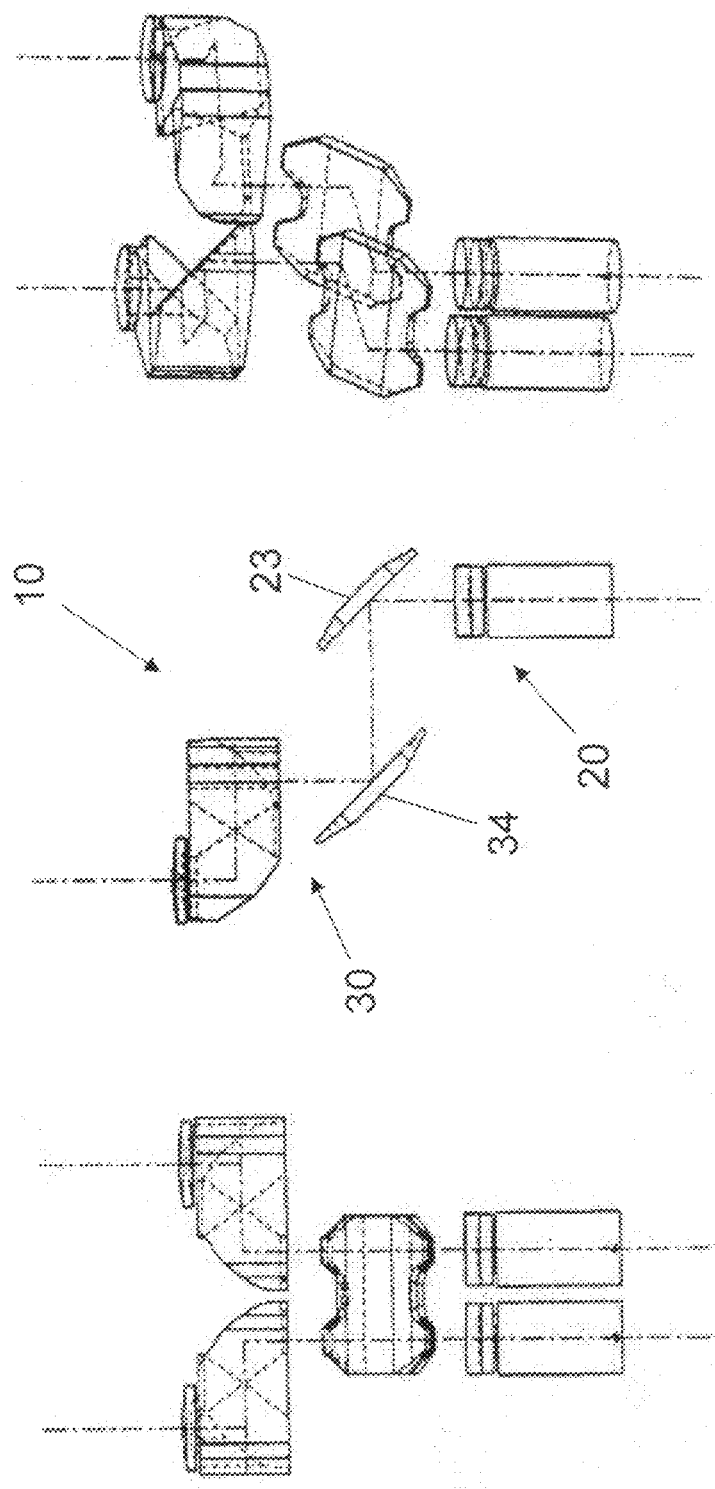

The invention will now be explained in more detail on the basis of embodiment examples with reference to the appended drawings. Here:

FIGS. 1 to 5 show, in schematic view, different viewing angles and viewing positions, which can be realized with the tube according to the invention;

FIGS. 6 to 11 show an example of embodiment of a tube according to the invention in different viewing positions;

FIGS. 12 and 13 show different angle interrelationships when a tube according to the invention is swung in;

FIG. 14 shows, in schematic view, another example of embodiment of a tube according to the invention in different viewing positions; and FIGS. 15 to 18 show, in schematic view, another example of embodiment of a tube according to the invention.

DETAILED DESCRIPTION OF THE INVENTION

In the figures, a tube is shown, which is designed as a swing-in tube 10, and which can be used for an optical observation device, for example, a microscope, e.g., an operating microscope.

The swing-in tube 10, which is shown in FIGS. 1 to 5, provides a base part 20, in which a deflecting element 23 disposed in a rotatable manner around an axis of rotation is provided in the form of a tilted mirror. In addition, an eyepiece support 30 with an uptake 31 for the eyepiece is provided, wherein eyepiece support 30 also has a deflecting element 34 in the form of a tilted mirror which is disposed in a rotatable manner around an axis of rotation. The two tilted mirrors 23, 34 are both disposed in a translatory as well as a rotational manner independently of one another, so they can be displaced or rotated.

The tilted mirrors 23, 34 are turned around the corresponding axes of rotation, which are shown in greater detail in connection with FIGS. 6 to 11. The translatory displacement is produced according to FIGS. 1 to 5 within an X-Y coordinate system, wherein the Y coordinate also can be designed as an optical axis 26 of base part 20.

As is shown in FIGS. 1 to 5, different, ergonomic viewing positions can be realized for almost any viewing angle by the use of two tilted mirrors 23, 34 that can be swung in independently of one another.

Figure 1:
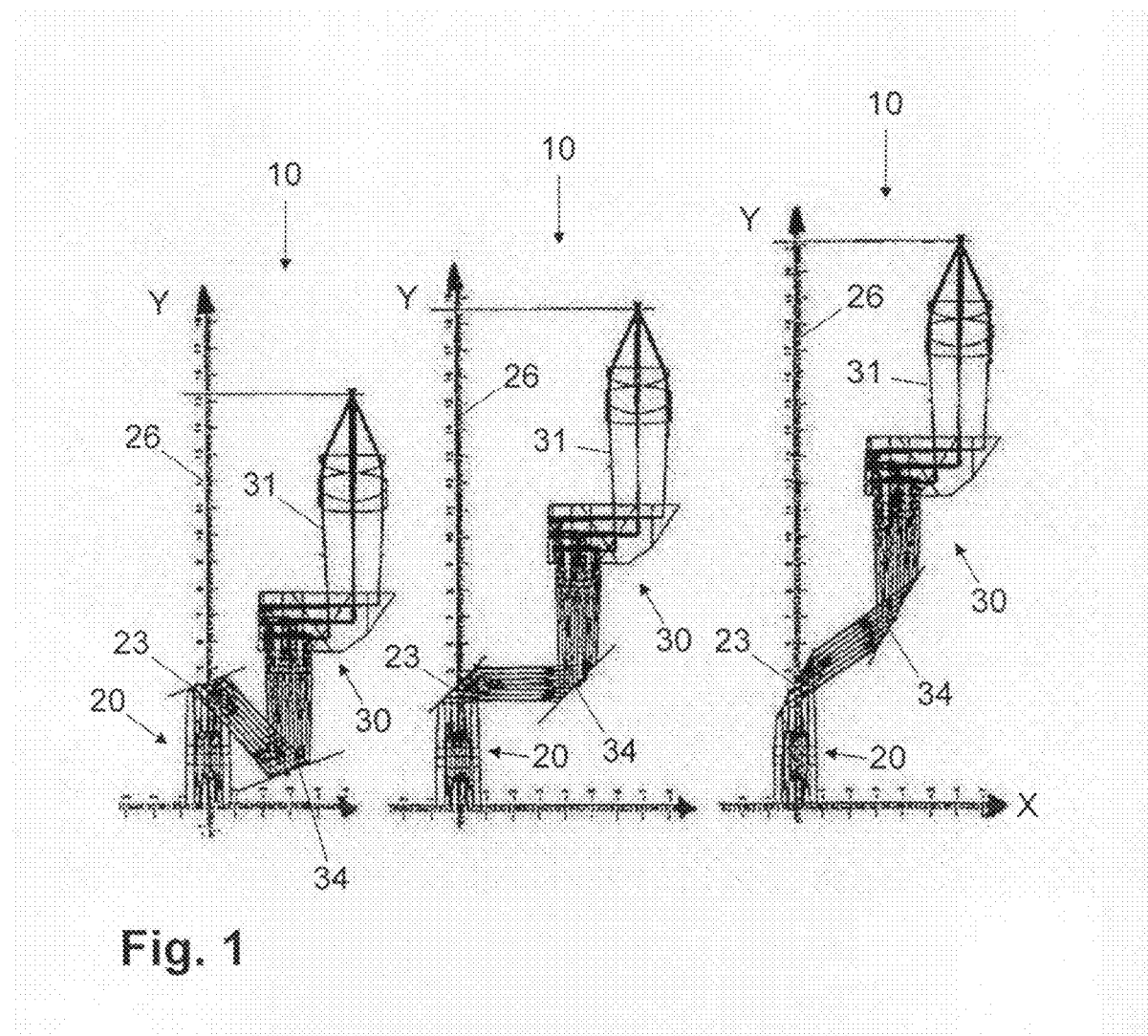
Figure 2:
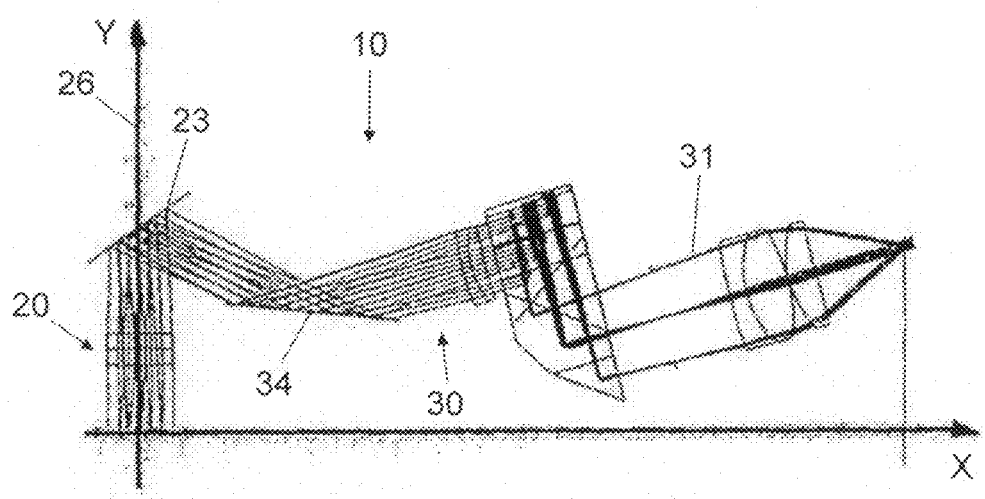
Figure 3:
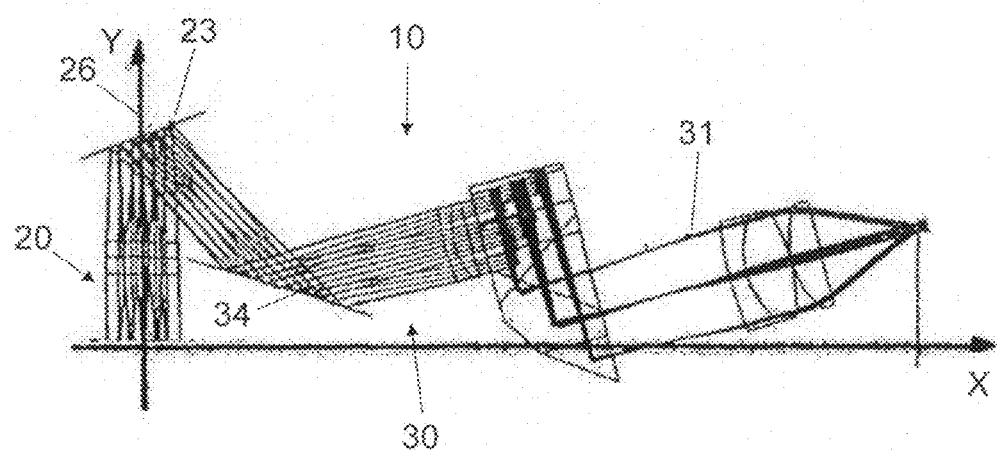
Figure 4:
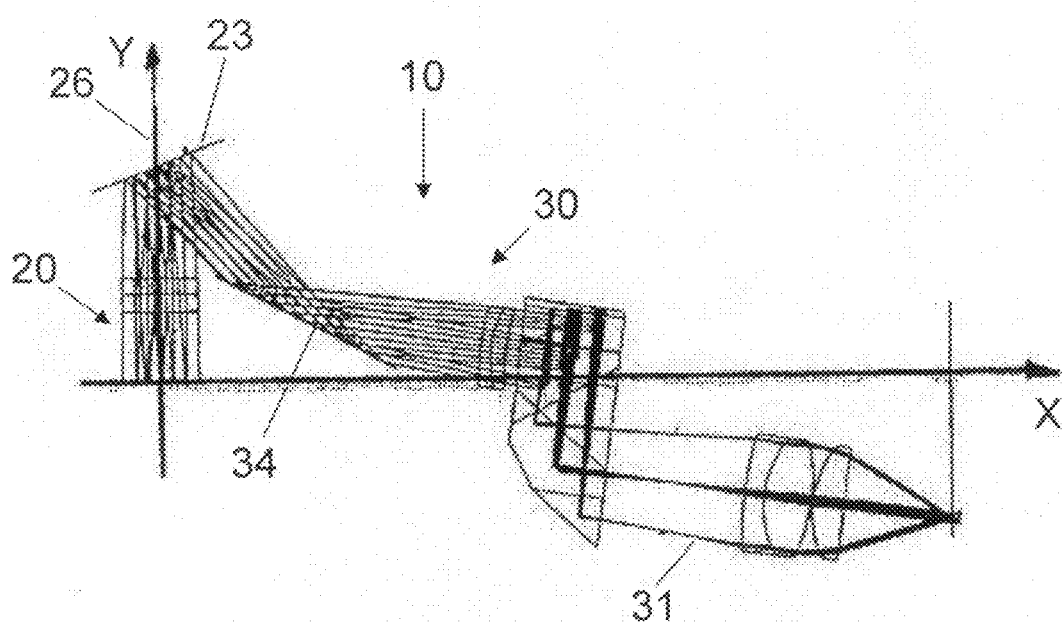
Figure 5:
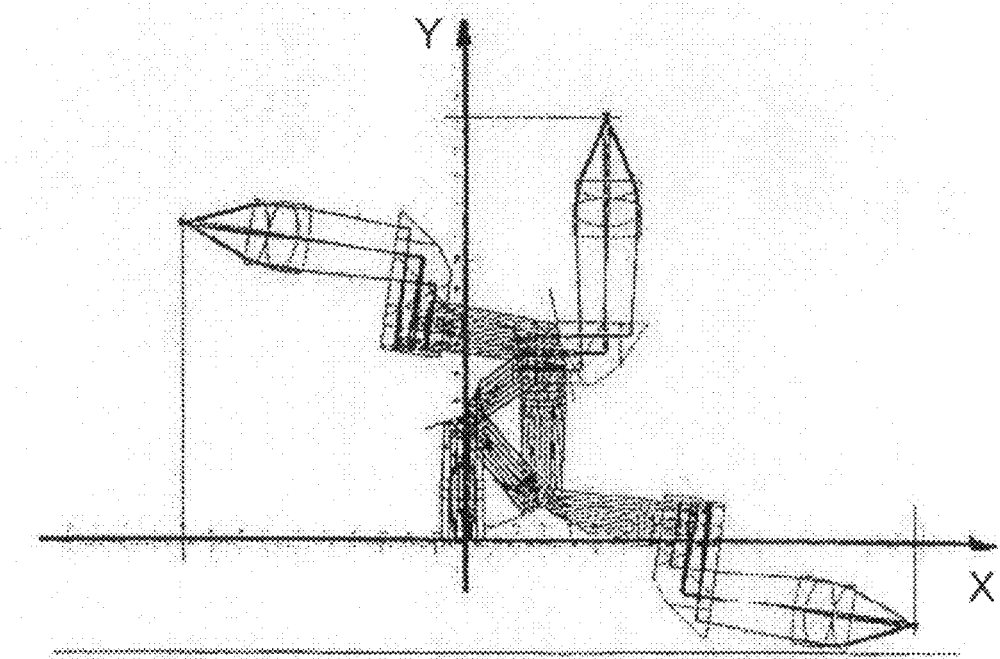
Figure 6:
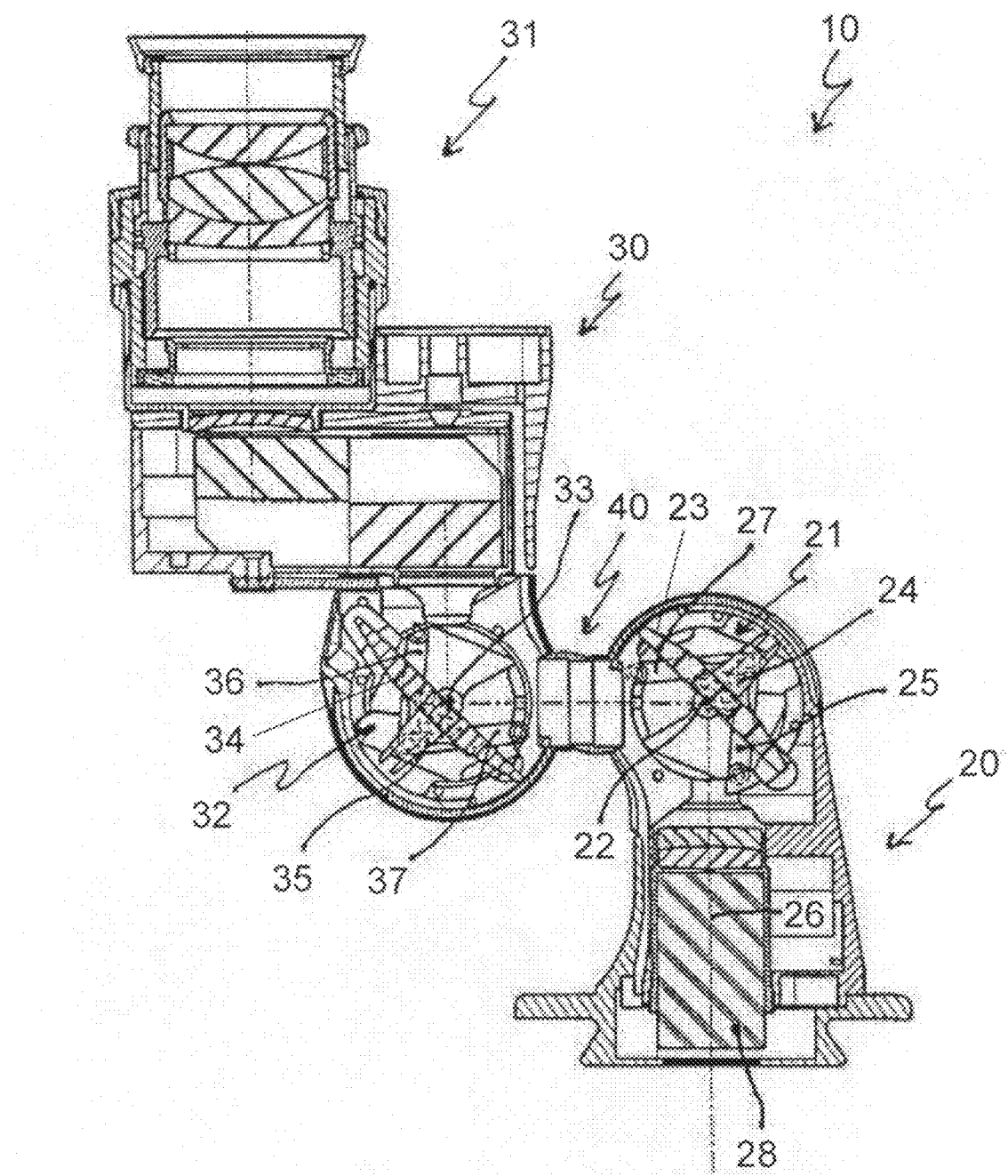

Three different structural lengths for direct viewing are shown in FIG. 1. In this case, the structural length can be varied, for example, by ±30 mm. FIGS. 2 and 3 show an oblique view with a viewing angle of 15° (this corresponds to a pivoting angle of 75°). FIG. 2 shows a tilting of the mirror according to a variant 1, whereas FIG. 3 shows a tilting of the mirror according to a variant 2. In comparison to variant 1, in the case of variant 2, the distance to axis 26 of the observation device is approximately 10 mm shorter. The viewing level is approximately 15 mm lower in comparison to variant 1. FIG. 4 shows a swung-in position with a viewing angle of −8° (which corresponds to a pivoting angle of 98°). Finally, in FIG. 5, a complete swinging range of swing-in tube 10 is shown, wherein this complete swinging range is 180° larger.

Figure 7:
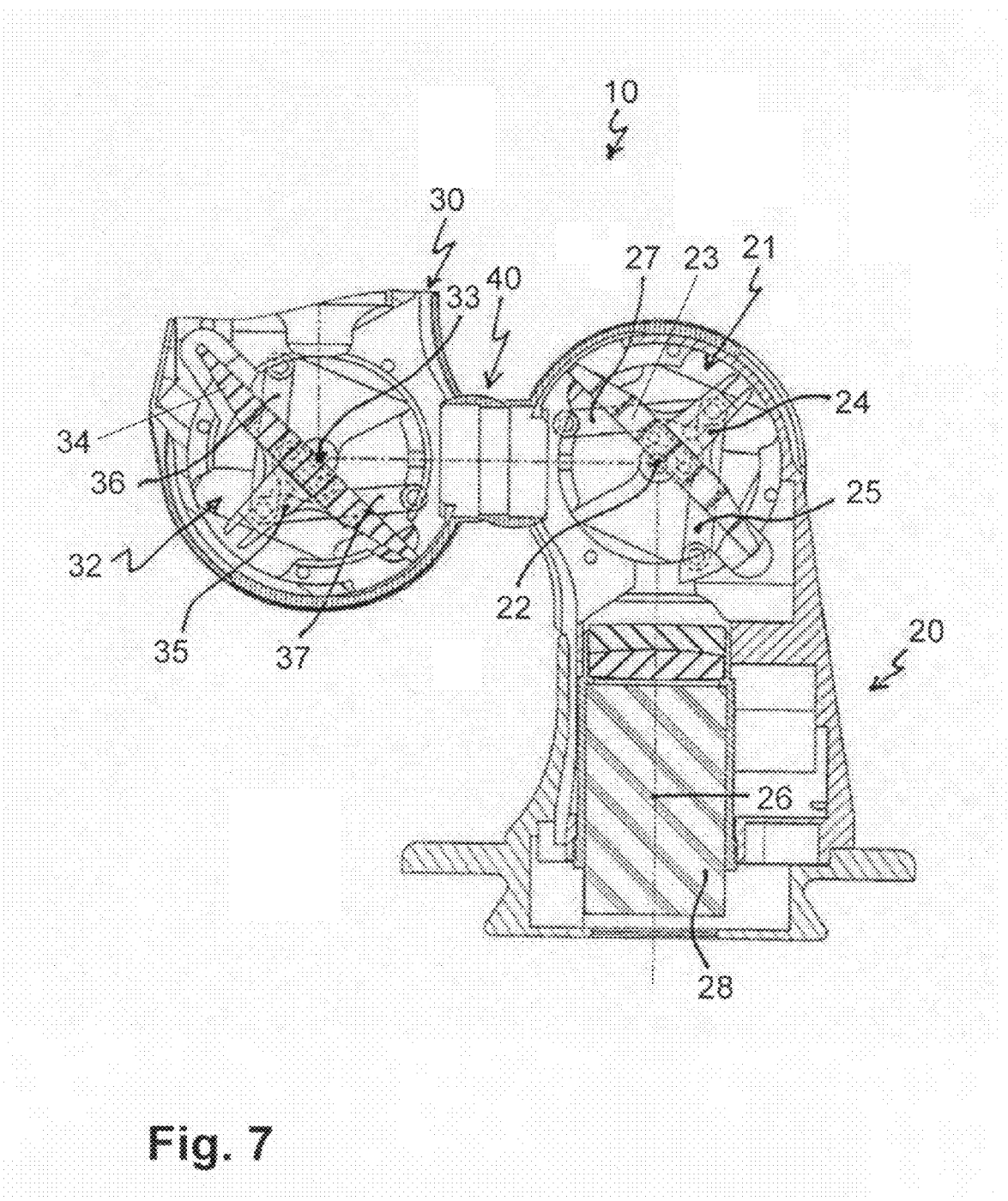
Figure 8:
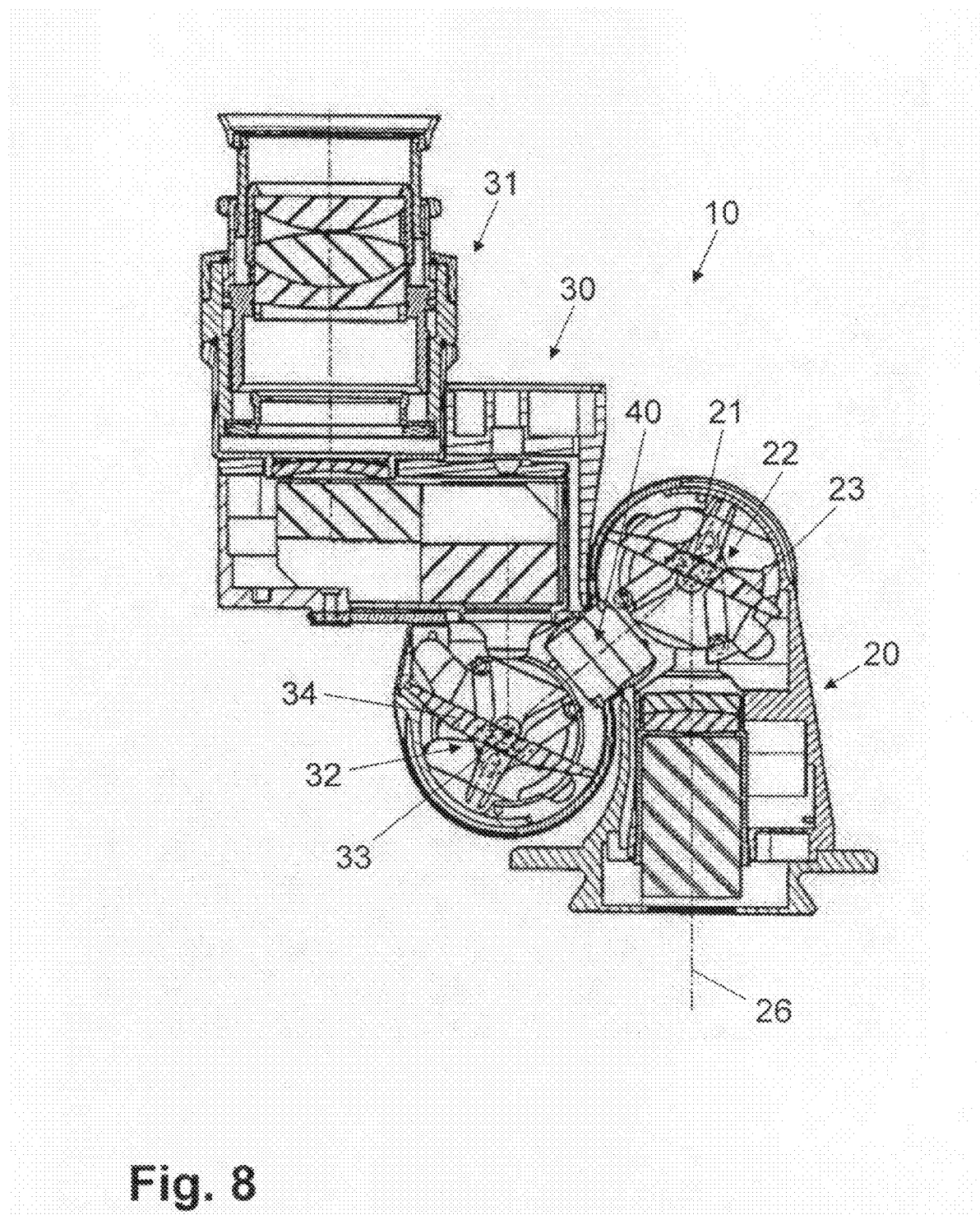
Figure 9:
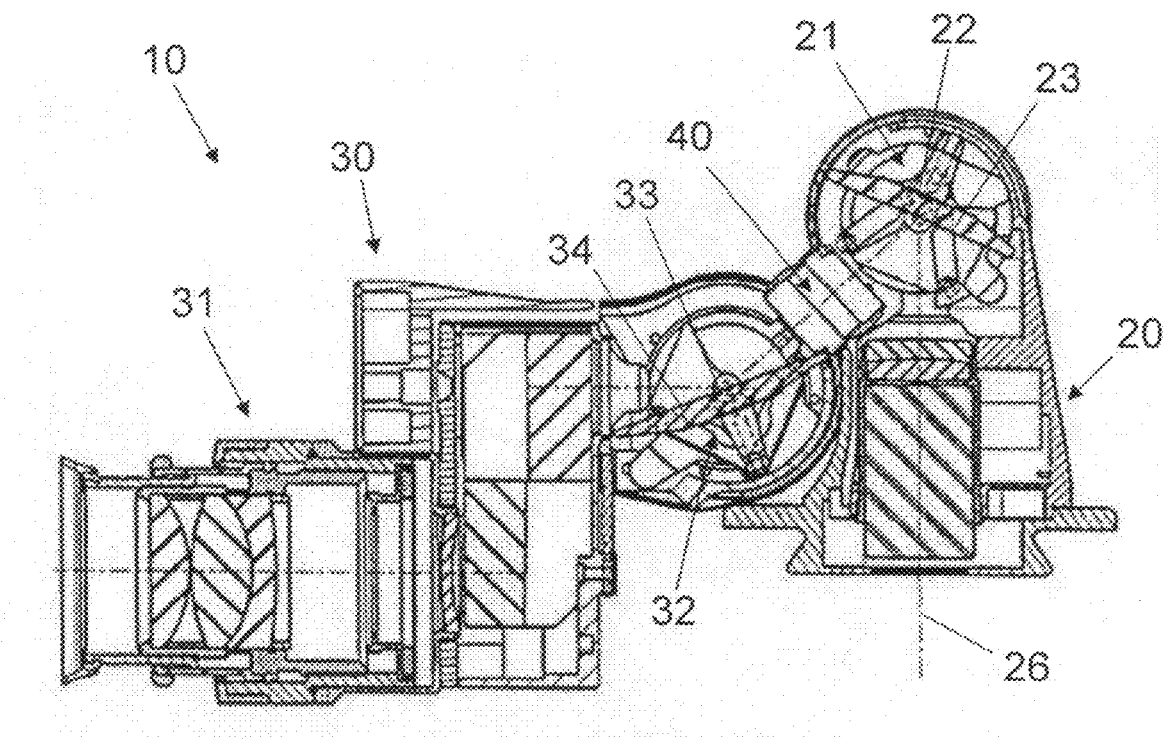
Figure 10:
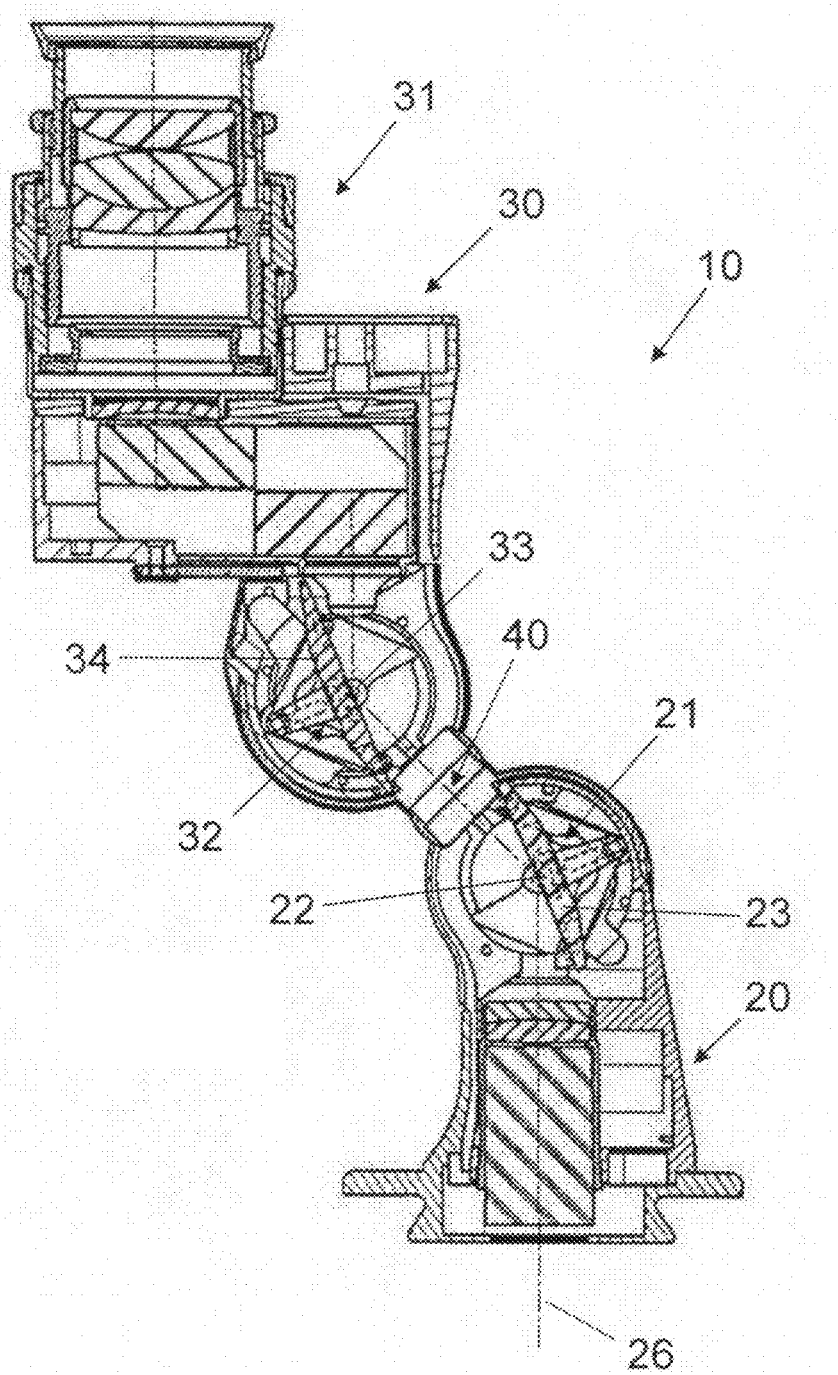
Figure 11:
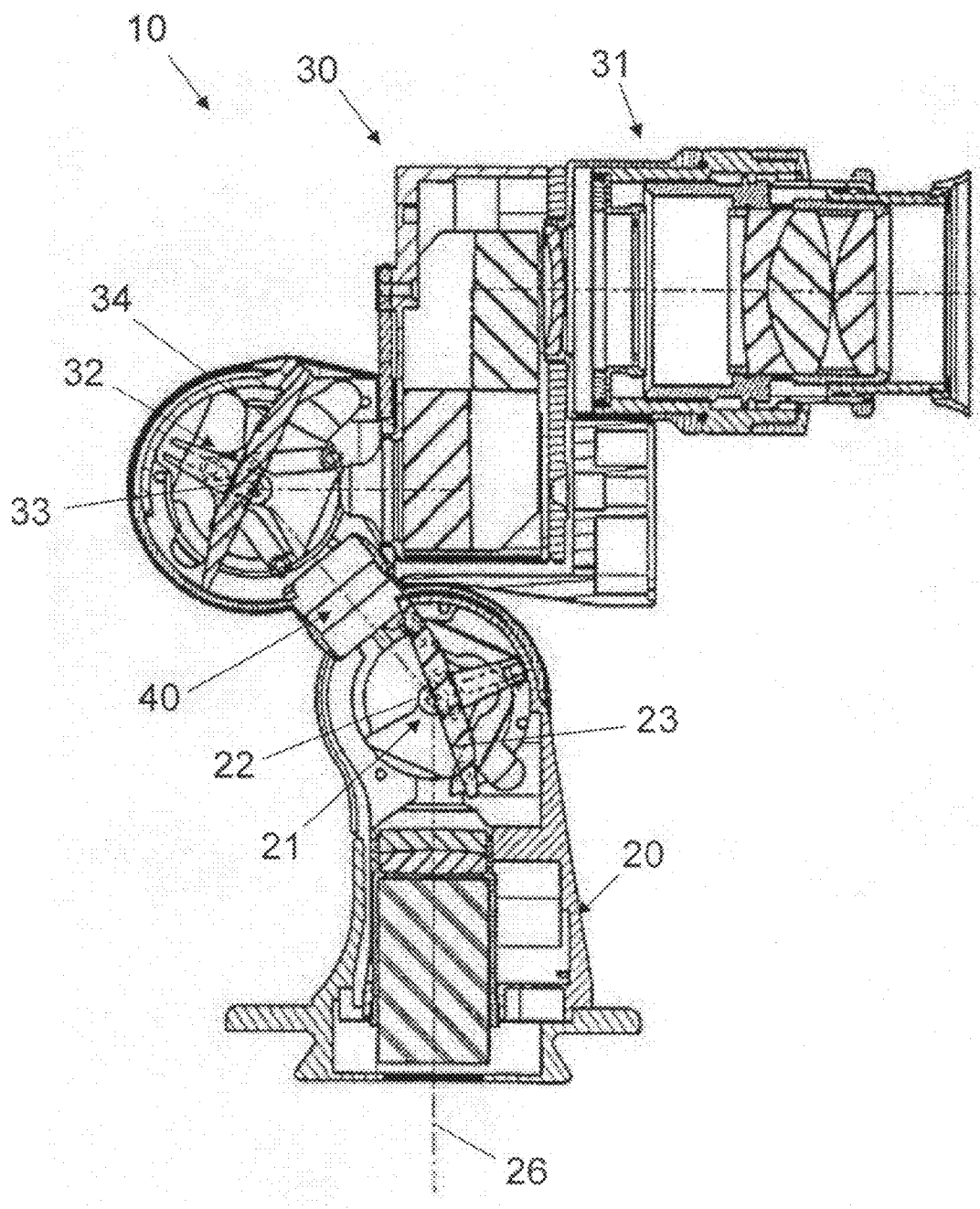

FIGS. 6 to 11 show an example of embodiment of a swing-in tube 10 according to the invention, wherein swing-in tube 10 is shown in different viewing positions in the individual figures. FIG. 7 shows here an enlarged excerpt of the swing-in tube 10 shown in FIG. 6.

Swing-in tube 10 first provides a base part 20, which is joined with an intermediate support 40 via a rotating joint 21. The intermediate support 40 is connected in turn, by means of a rotating joint 32, to eyepiece support 30, which bears an uptake 31 for the eyepiece.

Base part 20 further provides a deflecting element 23 in the form of a tilted mirror, which is likewise disposed in base part 20 so that it can rotate around an axis of rotation 22. In the present example, the axes of rotation of rotating joint 21 and of tilted mirror 23 are identical and are shown as a common axis of rotation 22. Axis of rotation 22 is disposed orthogonal to optical axis 26 of base part 20 and is joined with base part 20 and intermediate support 40.

Deflecting element 23 of base part 20 is coupled with rotating joint 21 between base part 20 and intermediate support 40. This is carried out via a special fork-shaped coupling element 24, which is joined with tilted mirror 23. This coupling element 24 is connected to a driver element 25, which is joined with base part 20. In addition, coupling element 24 is joined with a driver element 27, which is connected to intermediate support 40. Now, if base part 20 or intermediate support 40 is rotated, driver elements 25, 27 and coupling element 24 engage, so that tilted mirror 23 is entrained along with them, preferably by half of the angle of rotation.

Further, in its region which serves for mounting to the optical observation device, base part 20 may have a glass plate, which, among other things, serves for protecting against contamination.

The eyepiece support 30 is similarly constructed. Eyepiece support 30 also provides a deflecting element 34 in the form of a tilted mirror, which is likewise disposed in eyepiece support 30 so that it can rotate around an axis of rotation 33. Axis of rotation 33 in the present example is disposed parallel to axis of rotation 22 and is joined with eyepiece support 30 and intermediate support 40. In the present example, the axes of rotation of rotating joint 32 and of tilted mirror 34 are identical and are shown as a common axis of rotation 33.

Deflecting element 34 of eyepiece support 30 is coupled with rotating joint 32 between eyepiece support 30 and intermediate support 40. This is carried out also via a special fork-shaped coupling element 35, which is joined with tilted mirror 34. This coupling element 35 is joined with a driver element 36, which is joined with eyepiece support 30, and with a driver element 37, which is joined with intermediate support 40. Now, if eyepiece support 30 or intermediate support 40 is rotated, driver elements 36, 37 and coupling element 35 engage, so that tilted mirror 34 is entrained along with them, preferably by half of the rotating angle.

Different viewing positions or structural heights and structural lengths of swing-in tube 10 can now be realized for any viewing angle, as is shown in FIGS. 6 to 11.

Different angle interrelationships are shown in FIGS. 12 and 13 when a swing-in tube 10 according to the invention and which is configured in the way described above is swung in.

FIG. 12 shows a pivoting angle of 40° for the swing-in tube, whereas FIG. 13 shows a pivoting angle of −45°. In FIGS. 12 and 13, "AP" denotes the exit pupil, whereas "LAP" characterizes the positional range of the exit pupil. The reference "u" denotes the pivoting angle of the rotating joint 21 of base part 20 around axis of rotation 22, whereas "u/2" denotes the angle of rotation of tilted mirror 23 of base part 20 around axis of rotation 22. The reference "w" denotes the pivoting angle of the rotating joint 32 of eyepiece support 30 around axis of rotation 33, whereas "w/2" denotes the angle of rotation of tilted mirror 34 of eyepiece support 30 around axis of rotation 33. The following relationship exists between the pivoting angles of the base part, the intermediate support, and the eyepiece support: "tube pivoting axis=u−w".

As can be clearly seen in FIGS. 12 and 13, an advantageous configuration of swing-in tube 10 is then given, if tilted mirrors 23, 34 can rotate around the respective axes of rotation 22, 33 by an angle of rotation which corresponds to half of the angle of rotation of the corresponding rotating joints 21, 32 around the respective axes of rotation 22, 33.

Another example of embodiment of a swing-in tube 10 according to the invention is shown in FIG. 14. The swing-in tube which is shown therein provides three independent joints. Tube 10 in turn first has a base part 20 and an eyepiece support 30 for this purpose. Now, however, two intermediate supports 40 and 41 are found between these two components. The basic structure and the basic function of the tube correspond in other respects to the examples described in FIGS. 6 to 11, so that reference is made here to the full extent of the corresponding statements. FIG. 14 shows different viewing positions for tube 10.

Figure 16:
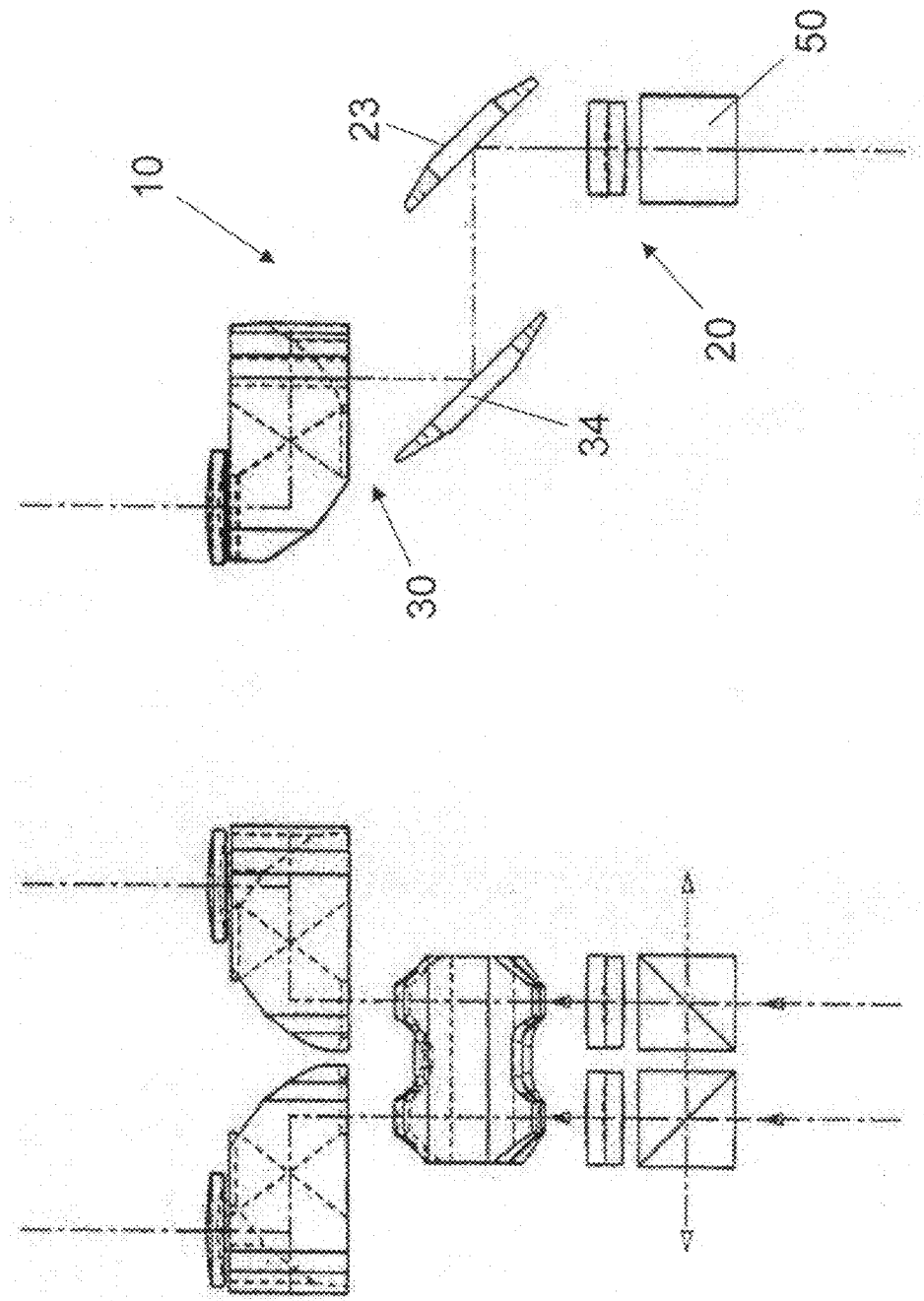

Finally, another example of embodiment for a swing-in tube 10 is shown in FIGS. 15 to 18, which corresponds in its basic structure and its basic function, of course, to tube 10 shown in FIGS. 6 to 11, so that in this respect, reference is made to the full extent of the corresponding statements. The tube is designed as a binocular tube and provides two separate beam paths for stereomicroscopy. In turn, tube 10 provides a base part 20, an eyepiece support 30 and two deflecting elements 23 and 34 that can be rotated independently of one another. Additionally, the tube according to FIG. 16 provides a decoupling element 50. The decoupling element 50 can be provided instead of glass plate 28 (see FIGS. 6 to 11) and can be designed as a divider element, e.g., as a splitter cube, splitter plate or similar dividing device. For example, it may be used for decoupling the beams for documentation devices. Such a decoupling element 50 is found in both beam paths of the microscope in FIG. 16. The direction of the decoupling is thus shown by corresponding arrows on the left side of FIG. 16.

Figure 17:
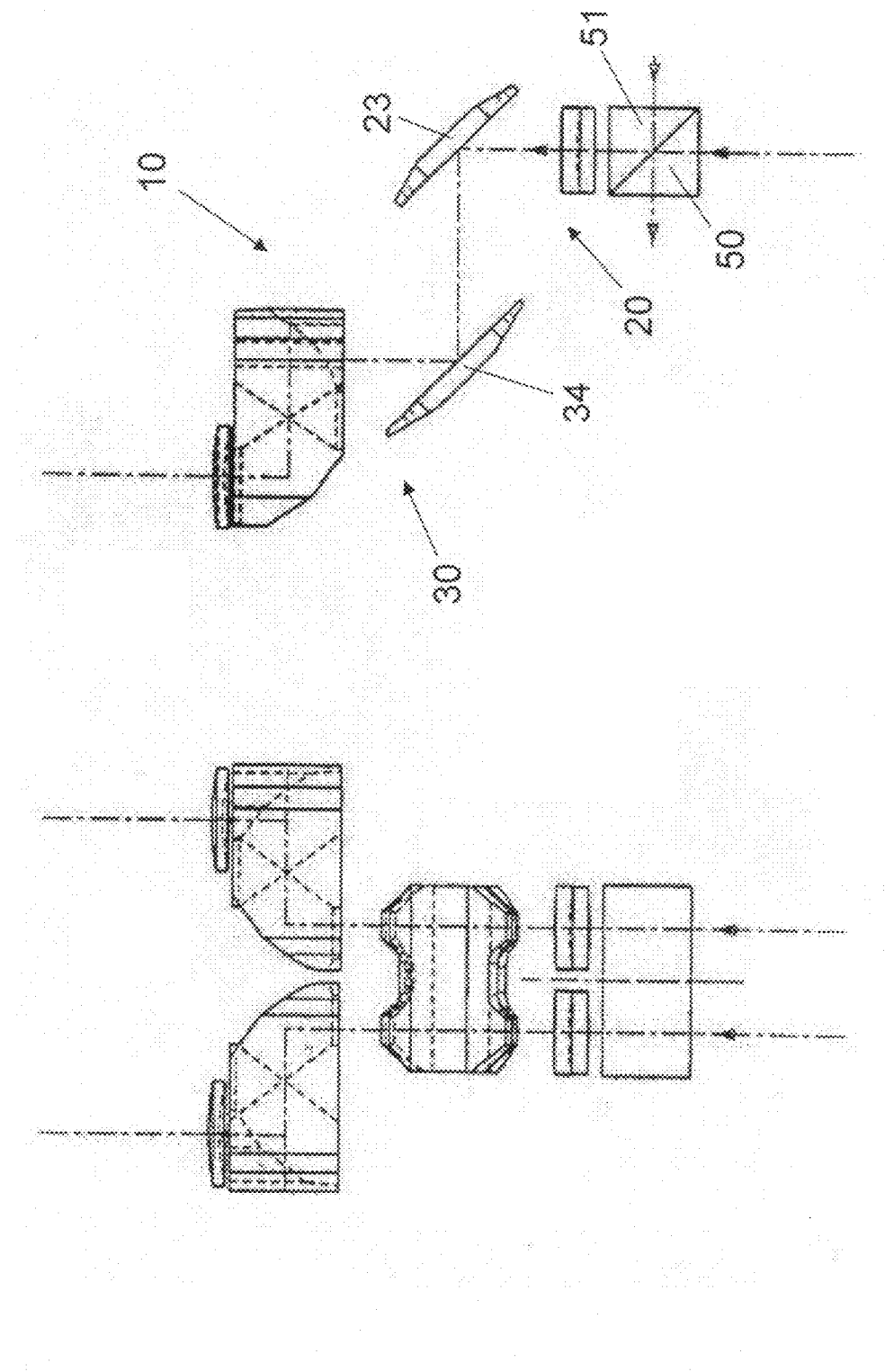
Figure 18:
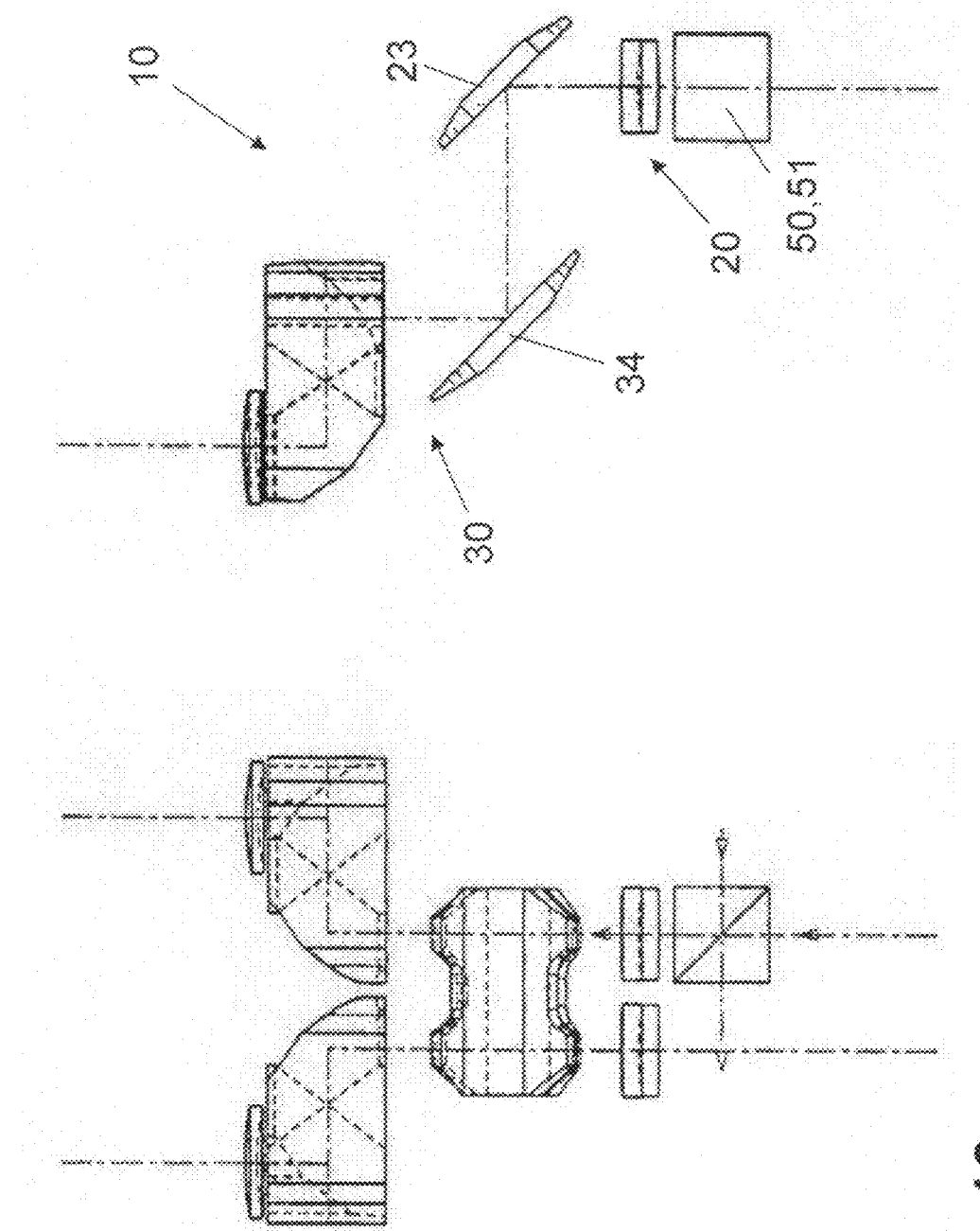

A solution is presented in FIG. 17, in which both a decoupling element 50 as well as a coupling element 51 are provided. The coupling element 51 can be designed like decoupling element 50 (see above), e.g., as a splitter cube, splitter mirror or similar dividing device. It can be used for the purpose of reflecting information from a data reflecting device into the beam path. In the example shown in FIG. 17, coupling elements 51 and decoupling elements 50 are also found in both beam paths of the observation device designed as a stereomicroscope. The direction of coupling and decoupling is thus shown by corresponding arrows on the right side of FIG. 17. The example shown in FIG. 18 corresponds in its basic structure to the example shown in FIG. 17, except that the coupling and decoupling elements 50, 51 are found only in one beam path in the example shown in FIG. 18.

LIST OF REFERENCE NUMBERS

10 Tube (swing-in tube)
20 Base part
21 Rotating joint
22 Axis of rotation
23 Optical element (deflecting element)
24 Coupling element
25 Driver element (base part)
26 Microscope axis
27 Driver element (intermediate support)
28 Glass plate
30 Eyepiece part
31 Uptake for the eyepiece
32 Rotating joint
33 Axis of rotation
34 Optical element (deflecting element)
35 Coupling element
36 Driver element (eyepiece support)
37 Driver element (intermediate support)
40 Intermediate support
41 Intermediate support
50 Decoupling element
51 Coupling element
AP Exit pupil
LAP Positional range of the exit pupil

The invention claimed is:

1. A tube for an optical observation device, having a viewing level that is linearly variable in length and/or height, wherein the tube has an optical light path, in which at least two optical elements are disposed, wherein at least two optical elements are disposed so that they can move independently of one another in the optical light path, wherein the tube has a base part, in which as an optical element a deflecting element is disposed so that it can rotate around a first axis of rotation, wherein the tube has an eyepiece support which can swing relative to the base part and in which as an optical element a deflecting element is disposed so that it can rotate around a second axis of rotation, wherein an intermediate support is provided which is joined with the base part and with the eyepiece support so that the eyepiece support can swing relative to the base part, via the intermediate support, wherein the intermediate support is joined with the base part via a rotating joint and with the eyepiece support via a rotating joint, wherein the deflecting element of the base part is coupled with the rotating joint which joins the base part and the intermediate support, and wherein the deflecting element of the eyepiece support is coupled with the rotating joint which joins the eyepiece support and the intermediate support, hereby characterized, that the deflecting element of the base part is connected to a coupling element, said coupling element cooperating with a driver element being connected to the base part, and with a driver element being connected to the intermediate support, and that the deflecting element of the eyepiece support is connected to a coupling element, said coupling element cooperating with a driver element being connected to the eyepiece support, and with a driver element being connected to the intermediate support.

2. The tube according to claim 1, further characterized in that it is designed such that the optical light path of the tube varies by less than 30% when the viewing level is varied.

3. A tube according to claim 1, wherein the tube is variably adjustable in its mechanical length.

4. The tube according to claim 1, further characterized in that the tube has a base element for mounting with an optical observation device.

5. The tube according to claim 4, further characterized in that at least one optical decoupling element and/or at least one optical coupling element is/are disposed in the base part.

6. The tube according to claim 1, further characterized in that the tube is designed as a swing-in tube.

7. The tube according to claim 1, further characterized in that the deflecting elements contain a translatory component.

8. The tube according to claim 1, further characterized in that the deflecting elements are disposed so that they can swing in, but are also rotationally independent of one another.

9. The tube according to claim 1, further characterized in that the deflecting element of the base part and/or the deflecting element of the eyepiece support is/are disposed in the region of a rotating joint.

10. The tube according to claim 9, further characterized in that the deflecting element of the base part and the rotating joint have an identical axis of rotation and/or that the deflecting element of the eyepiece support and the rotating joint have an identical axis of rotation.

11. The tube according to claim 10, further characterized in that the axis of rotation of the deflecting element of the base part is disposed parallel to the axis of rotation of the deflecting element of the eyepiece support.

12. The tube according to claim 1, further characterized in that the tube is designed for a monocular view or as a binocular tube.

13. The tube according to claim 1, characterized in that the tube is adapted for being used with a microscope.

14. The tube according to claim 1, characterized in that the deflecting element of the eyepiece support and the deflecting element of the base part are designed as tilted mirrors.

* * * * *